(12) United States Patent
Meehan (10) Patent No.: US 7,468,048 B2
(45) Date of Patent: Dec. 23, 2008

(54) JOINT ASPIRATE FACILITATING DEVICE

(75) Inventor: Richard Meehan, Centennial, CO (US)

(73) Assignee: National Jewish Health, Denver, CO (US)

( * ) Notice: Subject to any disclaimer, the term of this patent is extended or adjusted under 35 U.S.C. 154(b) by 116 days.

(21) Appl. No.: 11/539,578

(22) Filed: Oct. 6, 2006

(65) Prior Publication Data

US 2008/0086070 A1    Apr. 10, 2008

(51) Int. Cl.
*A61F 5/00* (2006.01)

(52) U.S. Cl. .......................................... 602/13; 602/26
(58) Field of Classification Search .................. 602/5, 602/13, 16, 20, 23, 26, 27; 128/882
See application file for complete search history.

(56) References Cited

U.S. PATENT DOCUMENTS

| | | | |
|---|---|---|---|
| 3,983,056 A | 9/1976 | Hosoda et al. | |
| 4,430,042 A | 2/1984 | House | |
| 4,438,950 A | 3/1984 | Hamisch, Jr. | |
| 4,489,718 A | 12/1984 | Martin | |
| 4,506,797 A * | 3/1985 | Bullock, III | 215/256 |
| 4,832,031 A | 5/1989 | Last | |

(Continued)

FOREIGN PATENT DOCUMENTS

TW         266026 Y    6/2005

(Continued)

OTHER PUBLICATIONS

International Search Report and Written Opinion for International (PCT) Application No. PCT/US07/80449, mailed Apr. 3, 2008.

(Continued)

*Primary Examiner*—Michael A. Brown
(74) *Attorney, Agent, or Firm*—Sheridan Ross P.C.

(57) ABSTRACT

A joint aspirate-facilitating device is provided including a flexible main panel that is secured to the joint to be aspirated. An inflatable bladder is secured to the main panel and is placed in contact with the soft tissues overlying and surrounding the joint space. The bladder is used to apply pressure to selected areas of the joint to compress the fluid sacs in the joint. An access opening is formed in the main panel designating the location where joint fluid is to be aspirated. The joint fluid is directed to flow to the area of the joint exposed at the access opening based on the shape of the bladder that compresses surrounding areas of the fluid sacs. A conventional hand pump may pressurize the bladder or the bladder may be filled with a viscous gel material to generate pressure. Multiple access openings may be formed on the main panel designating locations where aspiration is to be conducted. For multiple access openings, plugs may be used to fill those openings where aspiration is not conducted, thereby maximizing joint fluid flow only to the selected location where aspiration is to be conducted. An ultrasound probe may be attached and incorporated into the device to confirm joint fluid displacement into the targeted location prior to need aspiration. A disposable molded sterile dressing may applied to the access opening to reduce the risk of infections. The device can be used on any joint of the body, and the particular shape of the main panel and bladder accommodates maximum joint fluid flow to the point where aspiration is desired.

32 Claims, 11 Drawing Sheets

U.S. PATENT DOCUMENTS

| | | | |
|---|---|---|---|
| 4,872,448 A | 10/1989 | Johnson, Jr. | |
| 4,905,997 A | 3/1990 | Last | |
| 4,905,998 A | 3/1990 | Last | |
| 4,923,475 A | 5/1990 | Gosthnian et al. | |
| 4,938,207 A | 7/1990 | Vargo | |
| 4,947,834 A | 8/1990 | Kartheus et al. | |
| 4,953,543 A | 9/1990 | Grim et al. | |
| 4,960,115 A | 10/1990 | Ranciato | |
| 5,023,967 A | 6/1991 | Ferrand | |
| 5,038,938 A | 8/1991 | Berndt | |
| 5,078,128 A | 1/1992 | Grim et al. | |
| 5,088,478 A * | 2/1992 | Grim | 602/27 |
| 5,107,823 A | 4/1992 | Fratesi | |
| 5,138,729 A | 8/1992 | Ferrand | |
| 5,310,406 A | 5/1994 | Sharpe et al. | |
| 5,334,135 A | 8/1994 | Grim et al. | |
| 5,345,629 A | 9/1994 | Ferrand | |
| 5,352,189 A | 10/1994 | Schuman et al. | |
| 5,360,394 A | 11/1994 | Christensen | |
| 5,385,538 A | 1/1995 | Mann | |
| 5,395,379 A | 3/1995 | Deutchman et al. | |
| 5,407,421 A | 4/1995 | Goldsmith | |
| 5,411,541 A | 5/1995 | Bell et al. | |
| 5,415,625 A | 5/1995 | Cassford et al. | |
| 5,430,960 A | 7/1995 | Richardson | |
| 5,451,201 A | 9/1995 | Prengler | |
| 5,458,565 A | 10/1995 | Tillinghast, III et al. | |
| 5,462,517 A | 10/1995 | Mann | |
| 5,464,385 A | 11/1995 | Grim | |
| 5,498,246 A | 3/1996 | Deutchman et al. | |
| 5,520,622 A | 5/1996 | Bastyr et al. | |
| 5,520,650 A | 5/1996 | Zadini et al. | |
| 5,542,911 A | 8/1996 | Cassford et al. | |
| 5,582,584 A | 12/1996 | Billotti | |
| 5,613,941 A * | 3/1997 | Prengler | 602/13 |
| 5,620,411 A | 4/1997 | Schumann et al. | |
| 5,626,557 A * | 5/1997 | Mann | 602/26 |
| 5,634,904 A * | 6/1997 | Battenfield | 604/116 |
| 5,681,270 A | 10/1997 | Klearman et al. | |
| 5,695,452 A * | 12/1997 | Grim et al. | 602/6 |
| 5,701,370 A | 12/1997 | Muks et al. | |
| 5,785,673 A | 7/1998 | Billotti | |
| 5,792,084 A | 8/1998 | Wilson et al. | |
| 5,802,640 A | 9/1998 | Ferrand et al. | |
| 5,823,981 A | 10/1998 | Grim et al. | |
| 5,846,063 A | 12/1998 | Lakic | |
| 5,857,995 A | 1/1999 | Thomas et al. | |
| 5,865,166 A | 2/1999 | Fitzpatrick et al. | |
| 5,906,016 A | 5/1999 | Ferrand et al. | |
| 5,906,017 A | 5/1999 | Ferrand et al. | |
| 5,925,056 A | 7/1999 | Thomas et al. | |
| 5,957,874 A | 9/1999 | Klein | |
| 6,010,474 A | 1/2000 | Wycoki | |
| 6,042,602 A | 3/2000 | Wells | |
| 6,127,597 A | 10/2000 | Beyar et al. | |
| 6,149,613 A | 11/2000 | Klein | |
| 6,200,286 B1 * | 3/2001 | Zamani | 602/64 |
| 6,253,376 B1 | 7/2001 | Ritter | |
| 6,256,787 B1 | 7/2001 | Tyler | |
| 6,312,398 B1 | 11/2001 | Cencer | |
| 6,374,408 B1 | 4/2002 | Tomlinson et al. | |
| 6,438,776 B2 | 8/2002 | Ferrand et al. | |
| 6,497,673 B2 | 12/2002 | Rogalski | |
| 6,527,733 B1 | 3/2003 | Ceriani | |
| 6,551,280 B1 | 4/2003 | Knighton et al. | |
| 6,572,573 B1 | 6/2003 | Klein | |
| 6,585,774 B2 | 7/2003 | Dean, Jr. et al. | |
| 6,592,538 B1 | 7/2003 | Hotchkiss et al. | |
| 6,669,660 B2 | 12/2003 | Branch | |
| 6,761,726 B1 | 7/2004 | Findlay et al. | |
| 6,779,200 B1 | 8/2004 | Shah | |
| 6,782,640 B2 | 8/2004 | Westin | |
| 6,848,200 B1 | 2/2005 | Westin | |
| 6,866,717 B2 | 3/2005 | Shutic | |
| 6,939,502 B2 | 9/2005 | Lyden | |
| 6,941,598 B2 | 9/2005 | Ferrand | |
| 7,018,351 B1 | 3/2006 | Iglesias | |
| 7,041,641 B2 | 5/2006 | Rueger | |
| 7,056,179 B2 | 6/2006 | Courtney | |
| 2001/0014662 A1 | 8/2001 | Rueger | |
| 2001/0016646 A1 | 8/2001 | Rueger | |
| 2002/0143373 A1 | 10/2002 | Courtnage et al. | |
| 2003/0191437 A1 | 10/2003 | Knighton | |
| 2003/0226425 A1 | 12/2003 | Gotlib | |
| 2003/0229321 A1 | 12/2003 | Simon | |
| 2004/0220497 A1 | 11/2004 | Findlay | |
| 2005/0043660 A1 * | 2/2005 | Stark et al. | 602/19 |
| 2005/0096627 A1 | 5/2005 | Howard | |
| 2005/0101868 A1 | 5/2005 | Ridley | |
| 2005/0221383 A1 | 10/2005 | Liew | |
| 2005/0283124 A1 | 12/2005 | Simon | |
| 2006/0173426 A1 | 8/2006 | Urich | |
| 2006/0177475 A1 | 8/2006 | Rueger | |

FOREIGN PATENT DOCUMENTS

| | | | |
|---|---|---|---|
| WO | WO0219954 | | 3/2002 |
| WO | WO2006074257 | | 7/2006 |
| WO | WO2006084220 | * | 8/2006 |

OTHER PUBLICATIONS

Orthopedic Catalog of Braces and Supports Website Printout Entitled "Pneu Knee Airprene™ Pneumatic Knee Support", at http://bracesupport.com/kneu.htm, dated Oct. 6, 2006, 3 pages.

SROUFE Healthcare Products, LLC Website Printout Entitled "Home of the Patented PneuGel® Brand compression/cold therapy: (609) PneuGel Brand Knee Wrap", at http://www.pneugel.com/cgi-bin/sroufe/knee_supports.html, dated Sep. 7, 2006, 2 pages.

SROUFE Healthcare Products, LLC Website Printout Entitled "Home of the Patented PneuGel® Brand compression/cold therapy: PneuGel® Brand Products—Cold Compression Therapy for Where it Hurts", at http://www.pneugel.com/cgi-bin/sroufe/index.html, dated Sep. 7, 2006, 2 pages.

Contracture Management Knee Web Page Printout Entitled: "Pucci® Air-T Inflatable Knee . . . ", at http://www.deroyal.com/Catalog/Catalogs/NewProductPage.aspx?Catalog Code=COMPCA . . . , dated Sep. 7, 2006, 1 page.

\* cited by examiner

JOINT ASPIRATE FACILITATING DEVICE

FIELD OF THE INVENTION

The present invention relates to orthopedic devices used to support a joint, and more particularly, to an orthopedic appliance for facilitating aspiration of joint fluid in the knee or other joints such as the ankle or elbow.

BACKGROUND OF THE INVENTION

There are a number of orthopedic appliances that are used to support or immobilize various body parts. With respect to stabilizing or immobilizing the knee joint because of an injury, some of these orthopedic appliances include the use of inflatable air bladders for intermittently supporting and/or releasing support on the knee. One example of an inflatable knee brace includes U.S. Pat. No. 3,983,056, which describes inflatable tubes stitched into a fabric support extending vertically over a portion of the support. U.S. Pat. No. 4,430,042 describes a pillow type device strapped to the leg of a patient and then inflated. U.S. Pat. No. 4,872,448 discloses a U-shaped inflatable bladder placed over the patella. U.S. Pat. No. 4,938,207 describes a linear brace employing first and second fluid filled chambers. U.S. Pat. No. 4,947,834 describes a brace for compressing a patient's outer extremities, the brace including flexible chambers arranged in a series that are then successively inflated. U.S. Pat. No. 4,960,115 describes a body support apparatus having at least two inflation chambers. U.S. Pat. No. 5,626,557 discloses a knee brace having inflatable supports extending longitudinally on both sides of the knee.

The knee is perhaps the most common joint that is aspirated for purposes of diagnosing ailments of the joint. Such ailments may include infections, inflammatory or crystal arthritis, and others. The knee joint is also commonly aspirated for purposes of administering pharmaceutical agents into the knee joint such as glucocortocoids or visco-supplements. A medical practitioner attending to a patient having a knee joint ailment requires the practitioner to have certain skills in aspirating the knee, and a medical specialist such as an orthopedic surgeon or rheumatology specialist typically performs knee and other joint aspirations. A general practitioner rarely conducts knee aspirations without additional training. Accordingly, increased costs may be incurred because a medical specialist is typically required to conduct the procedure. Even with experienced specialists, knee aspirations can be difficult to perform because there is a very small area in which the aspirating needle can be inserted in the joint without striking pain-sensitive structures including bone or ligaments.

Therefore, there is a need to provide a device that eases the difficulty in performing a knee aspiration procedure, thereby increasing the odds of successfully performing the aspiration without inadvertently contacting surrounding tissue or bone. There is also a need to provide a device that allows general practitioners or other non-specialists to perform the procedure by increasing the size of the area where the needle may be inserted to penetrate the fluid sac surrounding the joint.

With respect to the prior art discussed above, while a number of inflatable knee brace configurations are known, none of the prior art devices provide adequate functionality for facilitating a joint aspiration procedure.

SUMMARY OF THE INVENTION

In order to overcome the various disadvantages inherent in conducting joint aspiration procedures, and to overcome the failure of the prior art to address such needs in the medical field, a joint aspirate-facilitating device is provided to enhance the capability of a medical practitioner to successfully perform a joint aspiration procedure. The device is made of a flexible, cloth-like material that incorporates an inflatable bladder. The bladder is specially sized and positioned to place pressure on specified regions of the joint to thereby displace distended joint fluid into a targeted location. The volume and pressure of the joint fluid is increased at the targeted location thereby increasing the size and pressure of the fluid sac where the aspirating needle can be placed to successfully aspirate the joint.

In a first embodiment, the joint aspirate-facilitating device resembles a traditional knee brace, but adopts unique structural features to facilitate a successful aspiration procedure. In this embodiment, the inflatable bladder is located to displace knee joint fluid from the contra lateral, superior, inferior and posterior joint regions towards a targeted location. An access opening is formed in the device at the targeted location. The aspirating needle penetrates the joint at the access opening, and the increased volume and pressure of the fluid located at the opening greatly enhances the ability of the practitioner to successfully penetrate the fluid sac. The access opening is preferably located either on the medial or lateral side of the knee joint, and is oriented to allow the medical practitioner to specifically access the suprapatellar bursae from the medial or lateral side.

The device of the present invention preferably incorporates a lightweight, washable fabric with a removable inflatable bladder controlled by an external, hand-operated pump to selectively pressurize the bladder. A pressure release element is provided to release or adjust pressure. A pressure gauge may be incorporated with the hand pump to allow the practitioner to monitor the amount of applied pressure. An internal pocket may be formed on an inner side of the device placed against the patient. The bladder is secured in this pocket during use. The bladder when deflated can be easily removed from the pocket to allow the device to be washed or otherwise serviced. A closure element, such as hook and pile material, may be used to secure both the internal bladder to the pocket as well as to tightly secure the device around the joint.

The device of the present invention can incorporate a disposable sterile field dressing to minimize risk of inadvertent inoculation of bacteria into the sterile cavity of the joint. In yet another embodiment of the invention, the access opening formed in the device can be used in a non-interventional procedure such as an ultrasound procedure to visualize the tissue located at the access opening. The device may include sleeves formed on the outer surface thereof to hold an ultrasound probe that is positioned at the access opening.

In one preferred embodiment, a single access opening can be provided at either the medial or lateral locations for aspirating a knee joint. In another embodiment, a pair of access openings can be provided at the medial and lateral locations, and depending whether a medial or lateral approach is taken, the unused access opening is blocked with a plug thereby encouraging fluid displacement from the opposite side of the joint.

Preferred embodiments are also disclosed for use of the device for other joints to include the wrist, elbow, and ankle. With these other embodiments, the basic principle of the invention is maintained: selective locational displacement of distended joint fluid to a targeted location, and providing an access opening in the device at the targeted location. The main portion of the inflatable bladder substantially encircles the joint when installed and the bladder therefore has a generally curved configuration. For the embodiments of the invention for use with the ankle and wrist joints, the main portion of the inflatable bladder may be generally cylindrical in shape when installed.

With the joint aspiration device of the present invention, the increased volume and pressure of the fluid to be aspirated increases the effective size of the targeted area, thereby reducing the chance that the aspirating needle will strike bone or will strike unintended tissue such as nerves or tendons. The device can be made in various sizes to accommodate joint sizes encountered with adults, children, or obese patients.

These and other features and advantages of the invention will become apparent from review of the following drawings, taken in conjunction with the detailed description.

DETAILED DESCRIPTION

Figure 1:
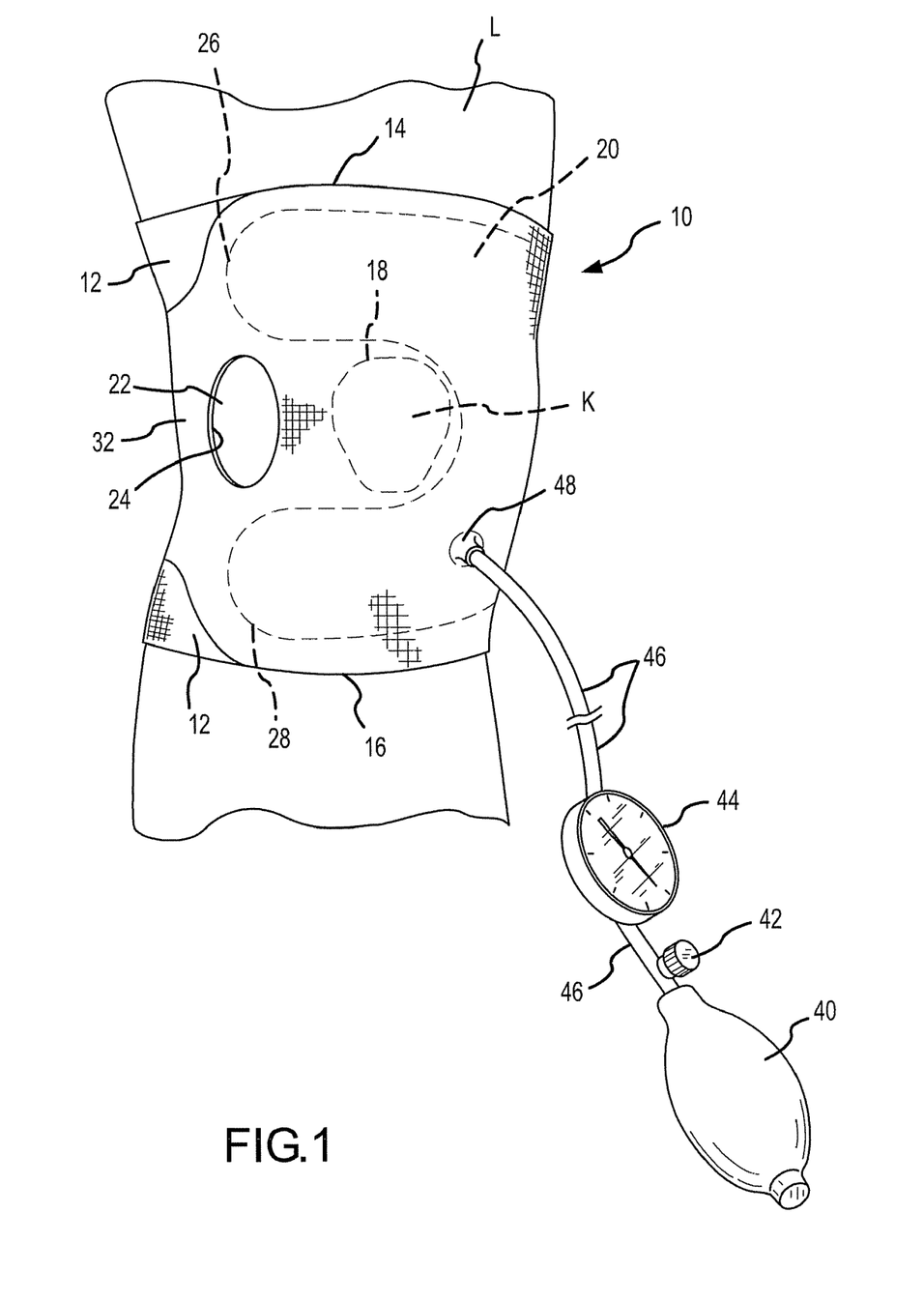
FIG. 1 is a perspective view of the joint aspirate-facilitating device of the present invention in a first embodiment for use with a knee joint.
Figure 2:
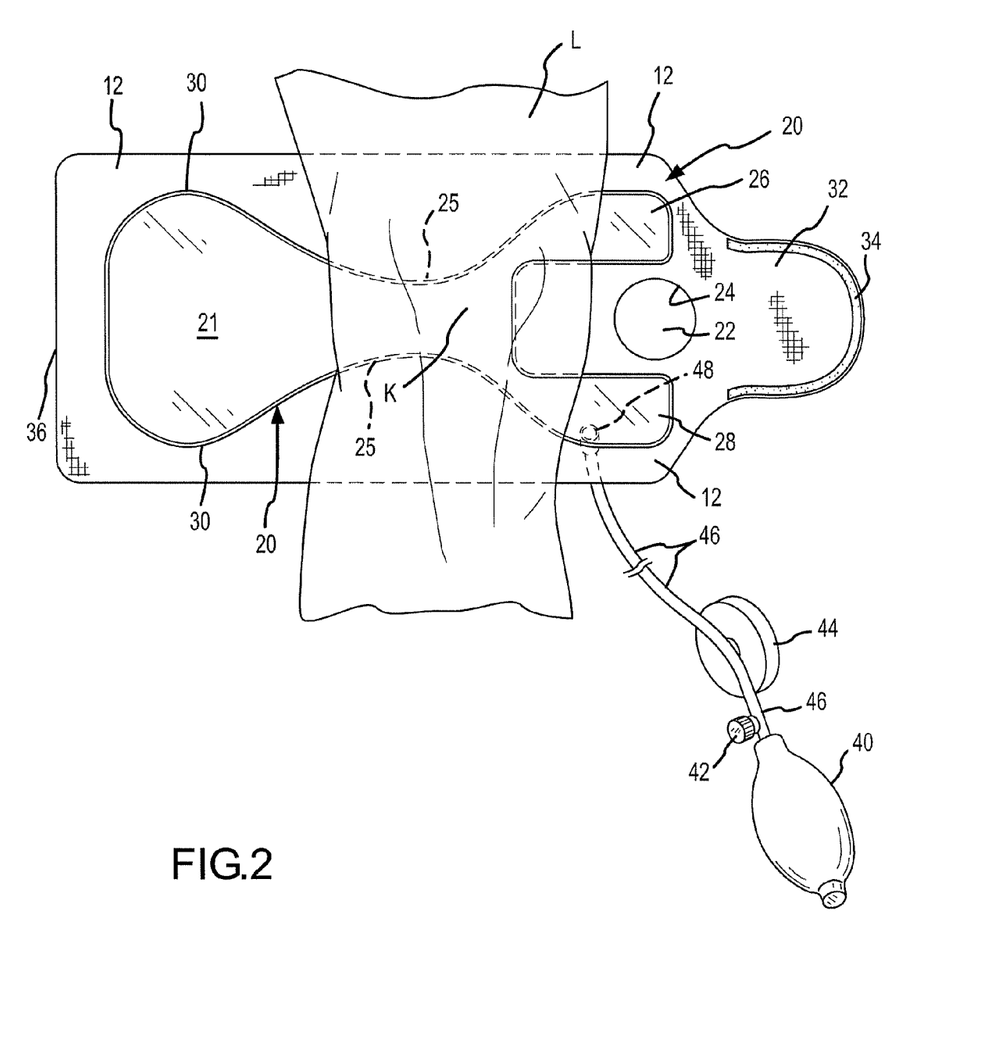
FIG. 2 is a plan view of the device of FIG. 1, illustrating the arrangement of the inflatable bladder and other details of the invention.

FIGS. 1 and 2 illustrate a first embodiment of the joint aspirating device of the present invention. In this embodiment, the device is used for facilitating aspiration of the knee joint. The aspirating device 10 includes a main panel or body 12 made of a flexible material that is wrapped around the joint. A bladder 20 is used to selectively apply pressure to the joint in order to cause joint fluid displacement to a targeted location. Preferably, the material is flexible but not elastomeric/elastic, since it is desirable to immobilize the joint so that the inflatable bladder 20 precisely displaces the joint fluid without deformation or stretching of the main panel. As shown, the main panel 12 is orientated with respect to the leg L of the patient so that upper and lower edges 14 and 16 extend transversely. One longitudinal side of the main panel 12 is defined by edge 36. The opposite longitudinal side is defined by flap 32 that is used to secure the device to the patient. As shown, the flap 32 includes a securing element 34, such as hook/pile material that attaches to corresponding hook/pile material (not shown) located on the backside of the main panel 12.

As shown, the bladder 20 includes first and second extensions 26 and 28 that surround the knee cap K, as well as a main portion 21 which extends around the back or anterior side of the knee joint and terminates at the opposite medial/lateral side of the knee joint. As shown, the main portion 21 has an area substantially larger than the area occupied by extensions 26 and 28. A converging or narrowed area 25 resides between the main portion 21 and the extensions 26 and 28. In this configuration, the bladder narrows at the posterior side of the joint so that the fluid sac is compressed but the muscular tissue around the posterior side is not. Since the joint capsule that contains synovial fluid does not usually extended into the muscle compartment and fascia, it is desirable to avoid applying pressure to the muscle masses that surround the knee joint, such as the quadriceps, gastrocnemius, biceps femoris, semitendonosis and semimembranosis muscle groups. Compressing these muscle groups can interrupt arterial blood flow or compress sensitive structures within the neurovascular bundle which is undesirable if the device must remain applied for any length of time. Therefore, the present invention contemplates that the bladder 20 can be adjusted in size and shape to best apply pressure to just the areas of the joint where the fluid sac(s) are located. A seam 30 denotes the line of connection between the bladder 20 and the main panel 12. An access opening 22 is formed in the main panel 12, and constitutes the targeted area where an aspirating needle is placed to aspirate fluid from the distended fluid-filled joint cavity. The opening 22 is defined by a circular edge 24. The access opening 22 can be sized and shaped to best locate the desired portion of the joint to be aspirated. FIGS. 1 and 2 may represent either the left or right leg, therefore, the access opening 22 is located either on the medial or lateral sides of the joint, depending upon which leg the device is applied to. It is also contemplated that the single access opening 22 can be located on the opposite medial or lateral side of the joint and accordingly, the orientation of the inflatable bladder would be reversed to accommodate the new location of the access opening. Thus, both medial and lateral sides of the knee joint for both the left and right legs can be exposed for aspiration through the selected position of the access opening A registration or alignment indicator is denoted by dotted line 18. This alignment indicator can be a line drawn on the exterior surface of the main panel and conforming in location and shape to the underlying kneecap when the device is installed. This alignment indicator helps the practitioner position the device on the joint so that the access opening 22 is located at an optimal position. The alignment indicator 18 is centered over the kneecap K for proper device alignment. Alternatively, the alignment indicator 18 can define another opening formed in the main panel 12 to expose the kneecap K that allows the medical practitioner to properly align the aspirating device. Further in the alternative, the alignment indicator 18 can be a patch of thinner material that allows the practitioner to better feel the location of the kneecap K in order to properly align the device. This thinner material can include a clear flexible plastic material that also allows the medical practitioner to view the kneecap. A seam 30 denotes the line of connection between the bladder 20 and the main panel 12.

FIGS. 1 and 2 also illustrate a pressurizing device 40 that enables a practitioner to pressurize the bladder. The pressurizing device 40 is shown in the form of a conventional hand held bulb similar to one used with a blood pressure monometer. An air line 46 interconnects the bladder 20 with the pressurizing device 40. A pressure release element 42 is also shown that enables the practitioner to selectively reduce the pressure, or completely deflate the bladder 20. As shown, the pressure release element 42 can be in the form of a conventional thumbscrew that connects to a needle valve (not shown) to relieve pressure through line 46. This thumbscrew/needle valve combination is also common with blood pressure manometers. An inline pressure gauge 44 is also illustrated that allows the practitioner to monitor the level of pressure maintained in the bladder.

The bladder 20 can also be filled with a viscous material such as a gel material, and pressurization of the joint would therefore occur without the need for supplying a pressurizing device 40. The particular viscosity and amount of the gel material can be chosen to apply a selected amount of pressure to the joint. For routine aspirations, it is possible to provide a bladder filled with the gel material to generate adequate pressure for displacing the joint fluid.

In FIG. 2, the bladder 20 makes direct contact with the patient. However, referring to FIG. 3, in order to provide greater comfort to the patient, it may be desirable to provide another layer of fabric material 23, thereby enclosing the bladder 20 in a pocket formed by the main panel 12 and the additional layer 23. Also, if it becomes necessary to wash or otherwise service the device, the bladder 20 may simply be removed from the pocket formed between the main panel and layer 23.

Figure 3:
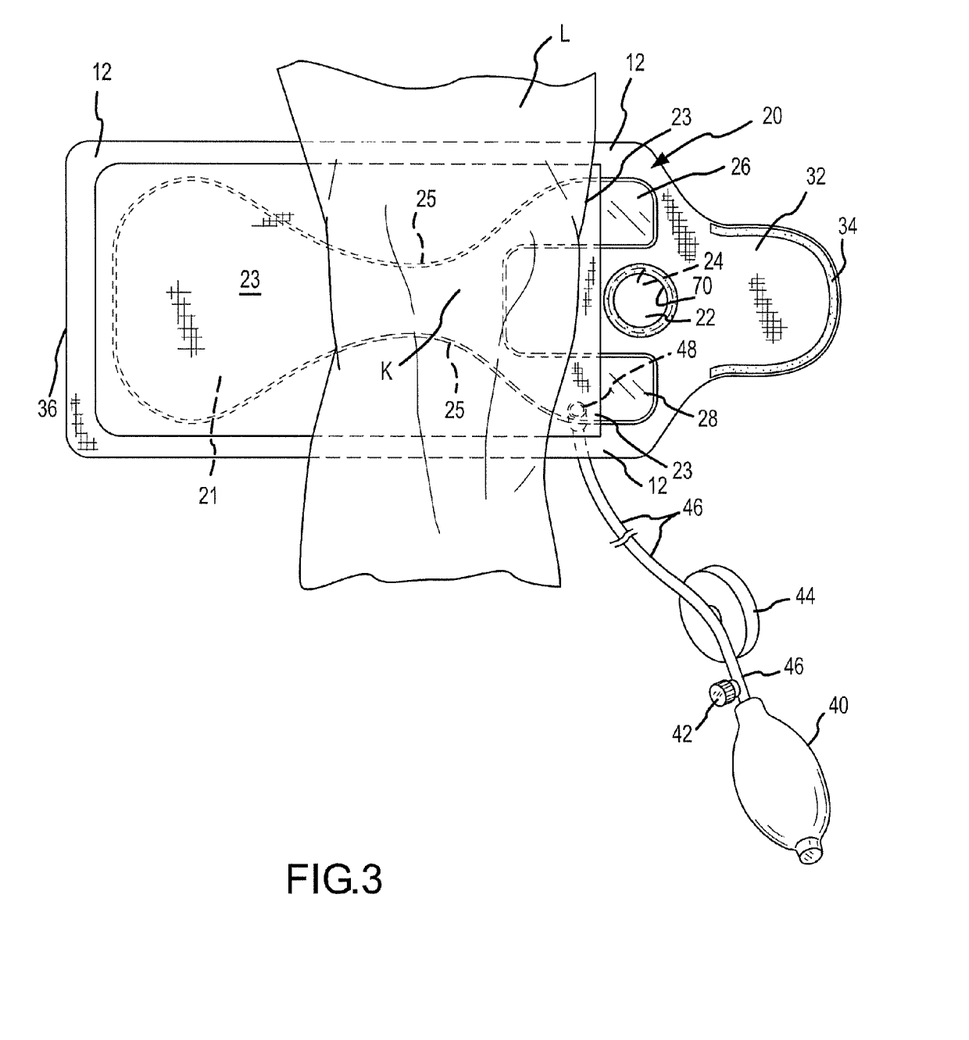
FIG. 3 is a plan view similar to FIG. 2, but further illustrating an interior liner forming a pocket for the bladder and a sterile disposable dressing placed around the access opening.

FIG. 3 also illustrates a ring shaped disposable sterile dressing 70 that can be used to cover the side edge 24 of the opening 22. By use of this sterile dressing 70, a sterile field may be maintained around the location of the patient where aspiration is to be conducted. The sterile dressing is simply replaced between procedures. Each of the embodiments may adopt the sterile dressing 70 as shown in FIG. 3.

Figure 4:
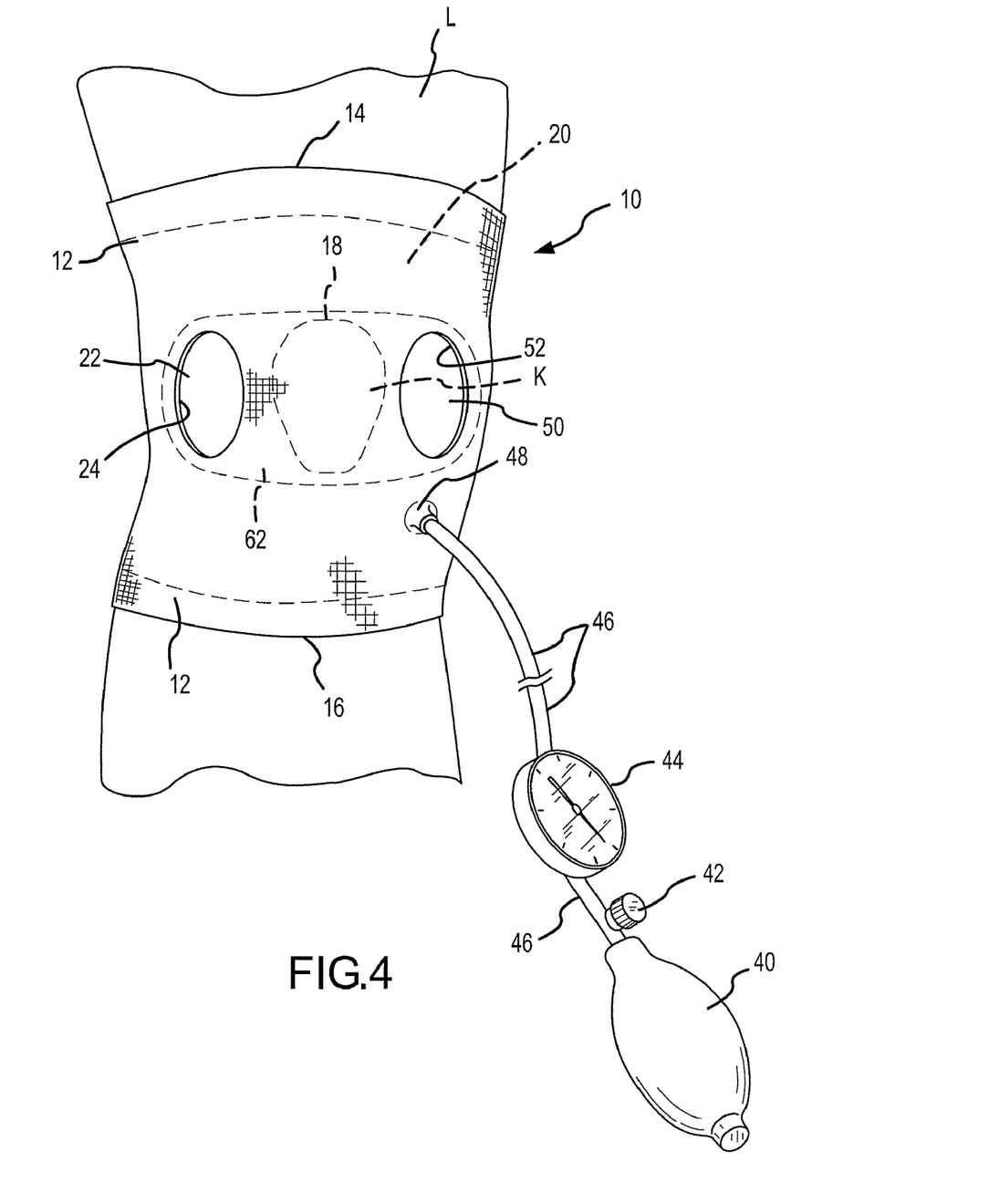
FIG. 4 illustrates a second embodiment of the present invention, wherein an access opening is provided on both the medial and lateral approaches to the knee joint.
Figure 5:
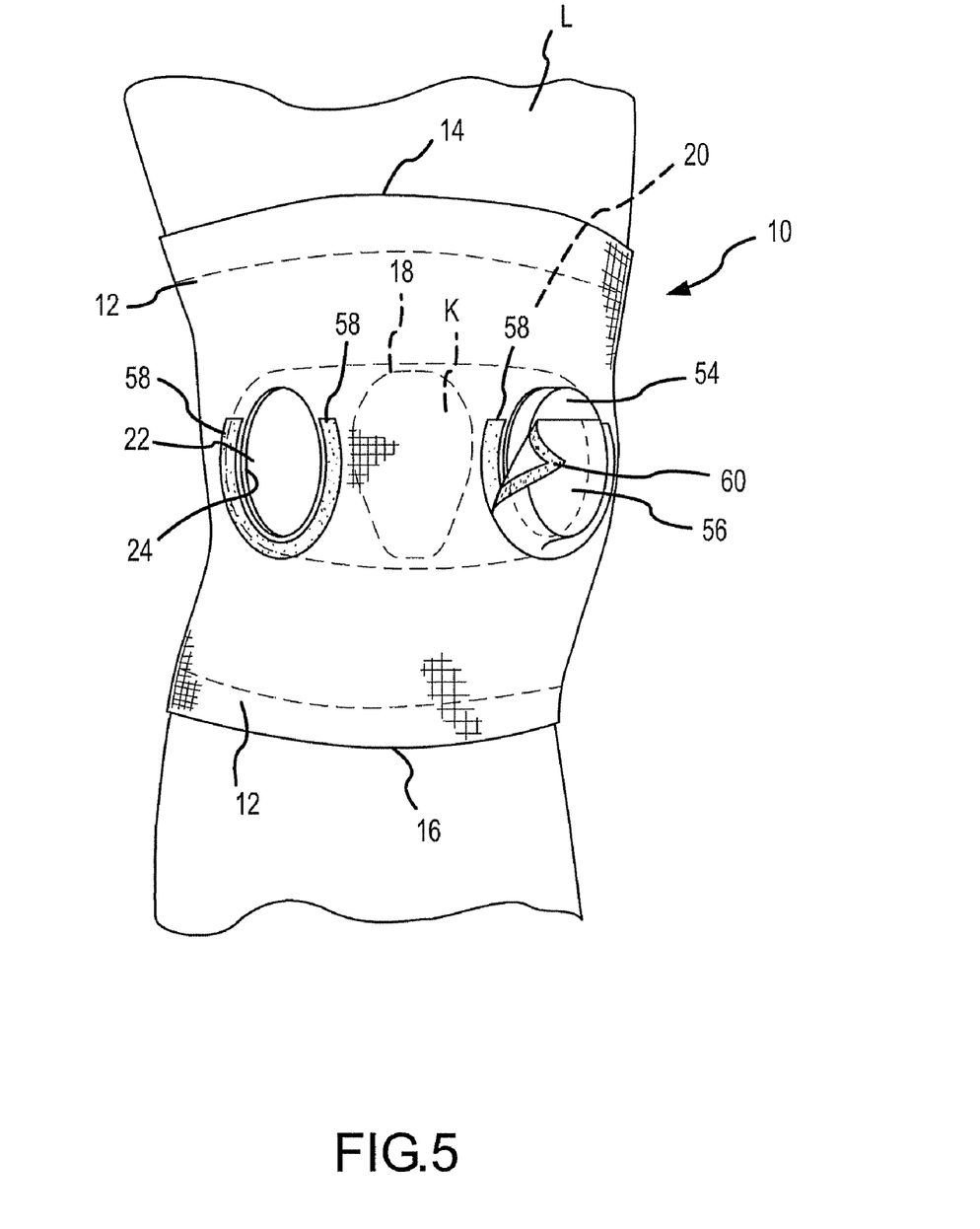
FIG. 5 is another perspective view of the embodiment of FIG. 4, illustrating incorporation of a removable plug that is placed to apply pressure to the side of the joint not being aspirated.
Figure 6:
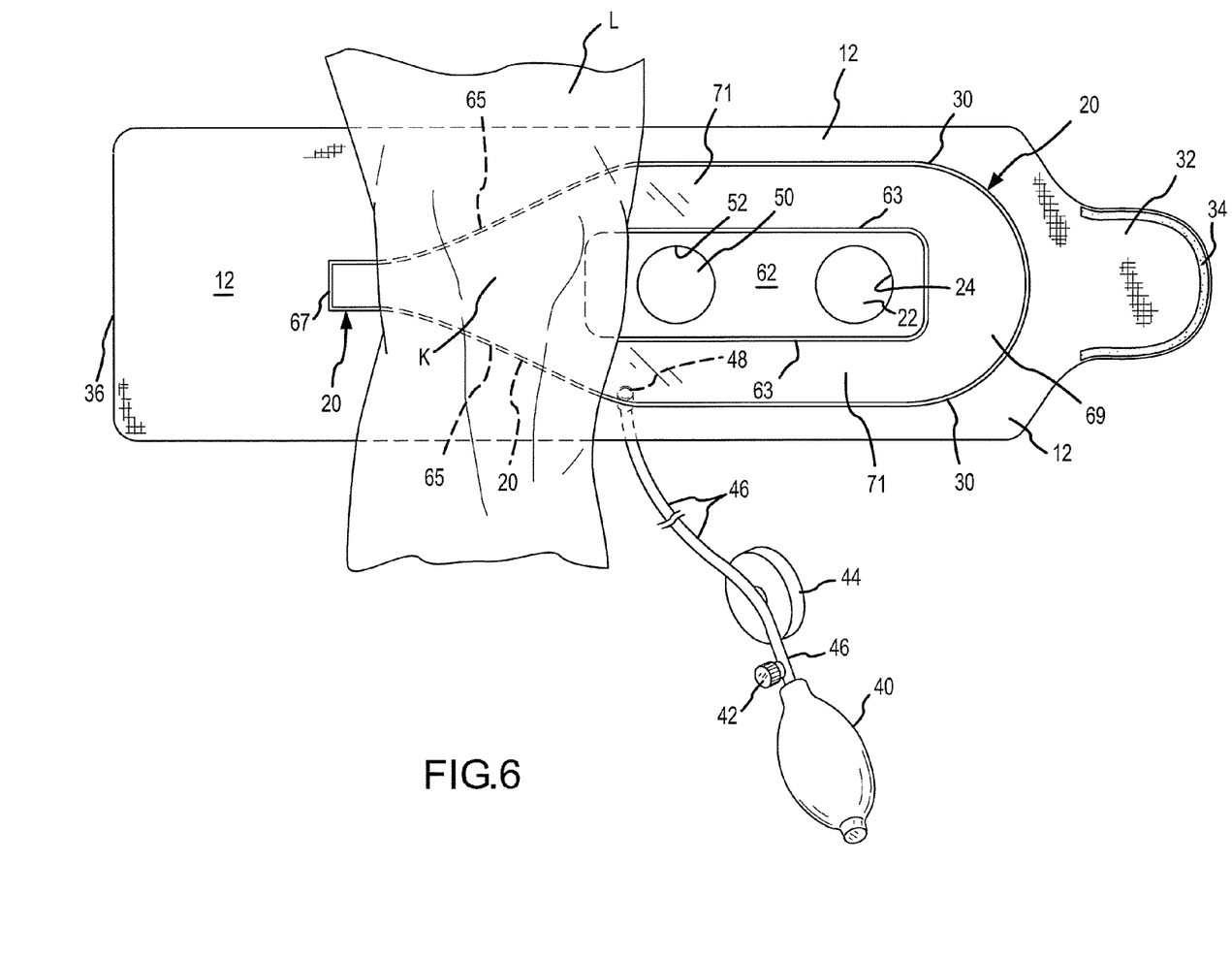
FIG. 6 is a plan view of the second embodiment of FIGS. 4 and 5.

FIG. 4 illustrates another embodiment of the present invention. In this embodiment, there are two access openings provided, one on each lateral/medial side of the kneecap K. As shown in this figure, the additional access opening 50 is defined by circular edge 52. With the embodiment of FIG. 4, the practitioner has the option of accessing either side of the joint; however, it is preferable to block the access opening not used to maximize pressure flow to the desired access opening. Accordingly, referring to FIG. 5, a pressurizing element or plug 54 may be used to pressurize the area of the joint not being accessed. As shown in FIG. 5, the plug 54 conforms in shape and size to the opening 22 or 50, and a closure flap 56 is used to secure the plug 54 to the main panel 12. The flap 56 may be secured by hook/pile material 60 that contacts hook/pile material 58 on the portion of the main panel surrounding the openings 22 and 50. As shown the hook/pile material 58 includes thin strips surrounding the openings 22 and 50. Preferably, the plug 54 has a selected thickness that allows a uniform pressure to be applied to the joint at the covered access opening. The shape of the bladder 20 in FIG. 6 is different than the shape of the bladder in the first embodiment. A central area 62 is devoid of any bladder material and is simply the main panel 12 at that area. Border or seam 63 defines termination of the bladder around the openings 22 and 50 at the central area 62. Thus, seam 63 also defines a central opening or aperture in the bladder to accommodate the openings 22 and 50. As also shown, one transverse side the bladder includes converging edges 65 that terminate at small end 67 to compress and displace the fluid from the posterior compartment thereby avoiding compression to the large muscle groups in this region. The other transverse side 69 is rounded in shape. The bladder extends between the transverse sides with a pair of spaced channels 71 as shown. Although FIG. 6 does not illustrate use of an additional layer of fabric material 23, it shall be understood that the inflatable bladder in this embodiment may be secured in a pocket formed by the additional layer 23 and the main panel like shown in the embodiment of FIG. 3. As mentioned above, the particular shape and size of the bladder may be adjusted to accommodate the particular joint to be aspirated.

Figure 7:
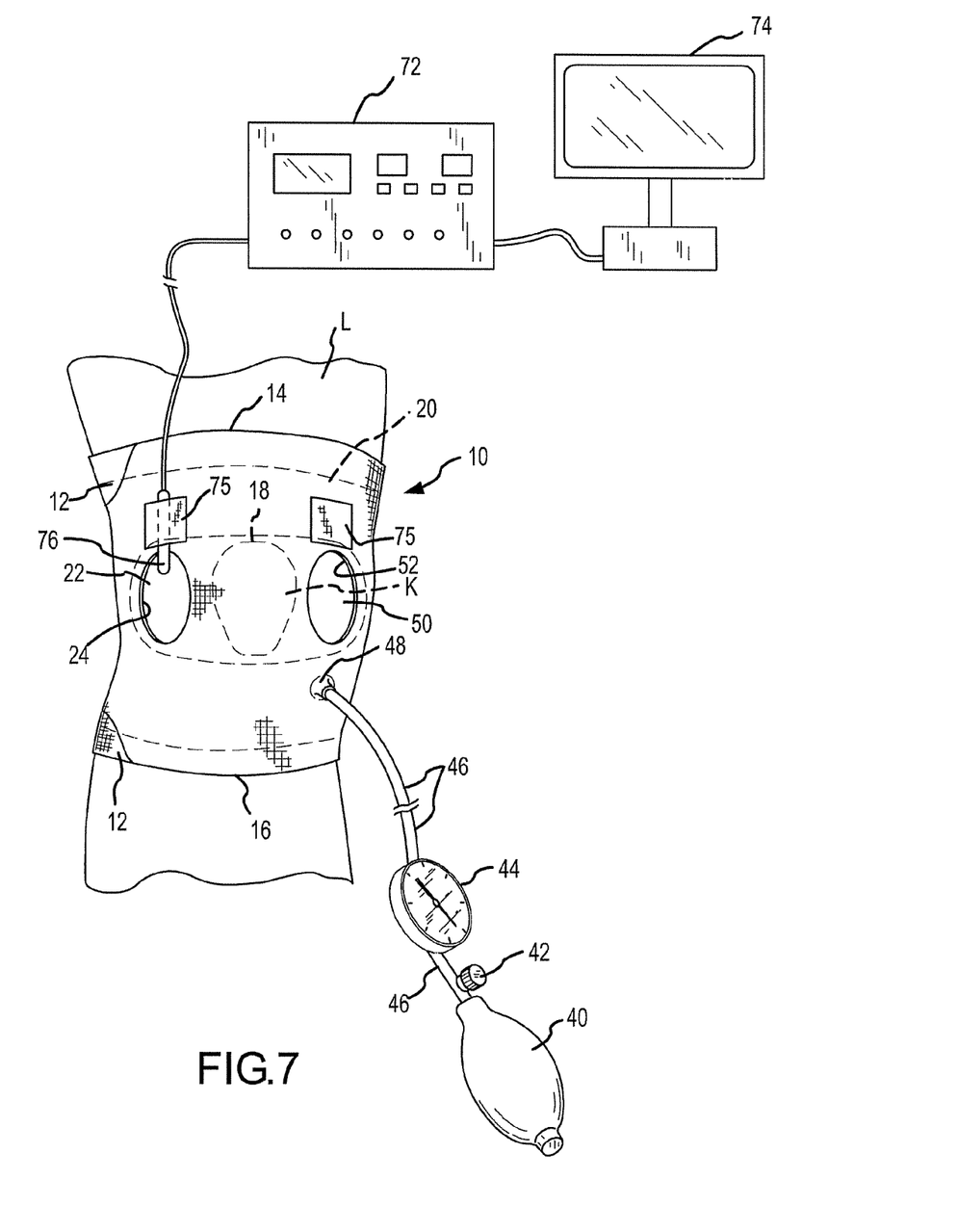
FIG. 7 is a perspective view of the embodiment of FIG. 4 in combination with an ultrasound imaging system and incorporation of sleeves on the outer surface of the device to position an ultra sound probe.

In accordance with another aspect of the present invention, it is also contemplated that an access opening 22/50 may be used for not only aspirating the joint, but for also conducting other invasive or non-invasive procedures. For example, prior to conducting the aspirating procedure, it may be desirable to confirm that the area exposed for aspiration at opening 22/50 does in fact contain fluid. Accordingly, a non-invasive procedure such as an ultrasound may be conducted where an ultrasound probe is placed on the patient at the opening 20/50. Referring to FIG. 7, the embodiment of FIG. 4 is shown in combination with an ultrasound system. Sleeves or pockets 75 can be formed in the main panel 12 to accept an ultrasound probe 76 used to visualize tissue at the opening 22/50. A conventional ultrasound unit 72 and a video monitor 74 are also illustrated.

Figure 8:
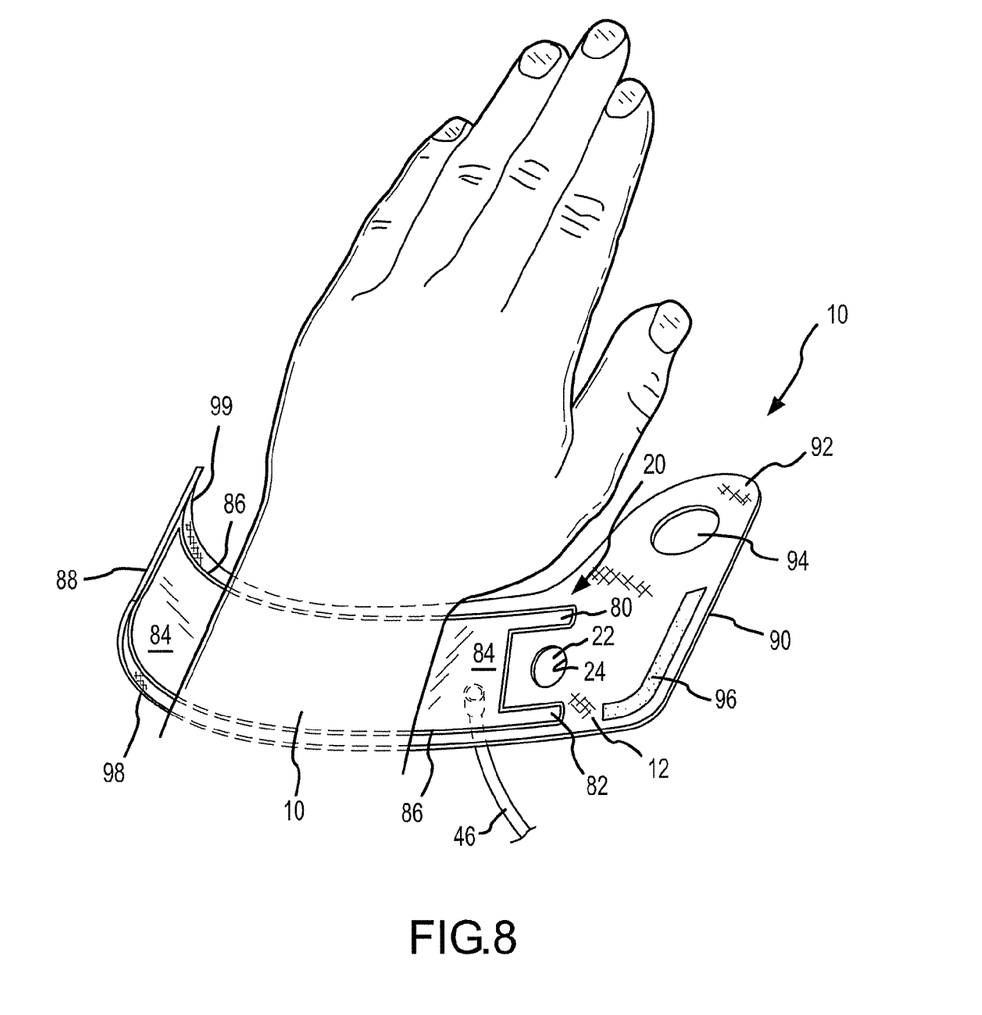
FIG. 8 is a perspective view of another embodiment of the present invention for use with the wrist joint.
Figure 9:
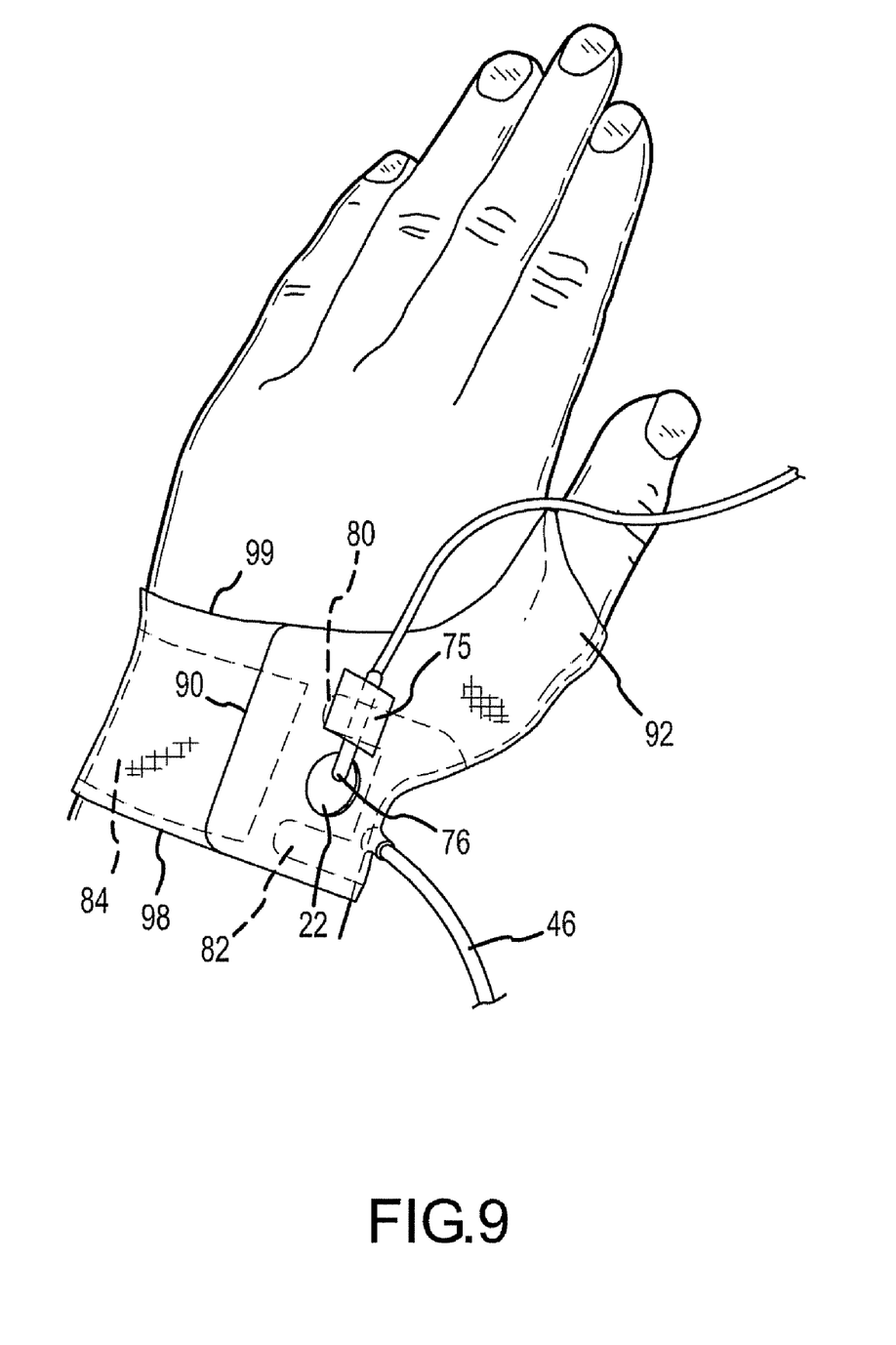
FIG. 9 is another perspective view of the embodiment of FIG. 8 showing the device installed on a patient's wrist.

FIGS. 8 and 9 illustrate another preferred embodiment of the present invention wherein the device 10 is especially adapted for use with the wrist joint W. In this embodiment, the main panel 12 is wrapped around the wrist joint, and extra support to the main panel is provided by a thumb extension 92 that includes a thumb opening 94. The shape of the main panel 12 is substantially rectangular except for the thumb extension 92. Accordingly, the main panel 12 in this embodiment is defined by an upper transverse edge 99, lower transverse edge 98, a first longitudinal edge 88, and a second longitudinal edge 90. The inflatable bladder 20 is also substantially rectangular shaped except for the extensions 80 and 82 that are positioned on both sides of the access opening 22. Seam 86 denotes the line of connection between the bladder 20 and the main panel 12. The main portion 84 of the inflatable bladder 20 provides a circumferential compression force around the wrist joint, thereby causing the joint fluid to be displaced and concentrated at the location of the access opening 22. Hook and pile material 96 is formed along the longitudinal edges in order to tightly wrap the device around the wrist W. As illustrated in FIG. 9, the device may also include a sleeve 75 that receives an ultrasound probe 76 so that an ultrasound procedure may be conducted to visualize tissue at the opening 22.

Figure 10:
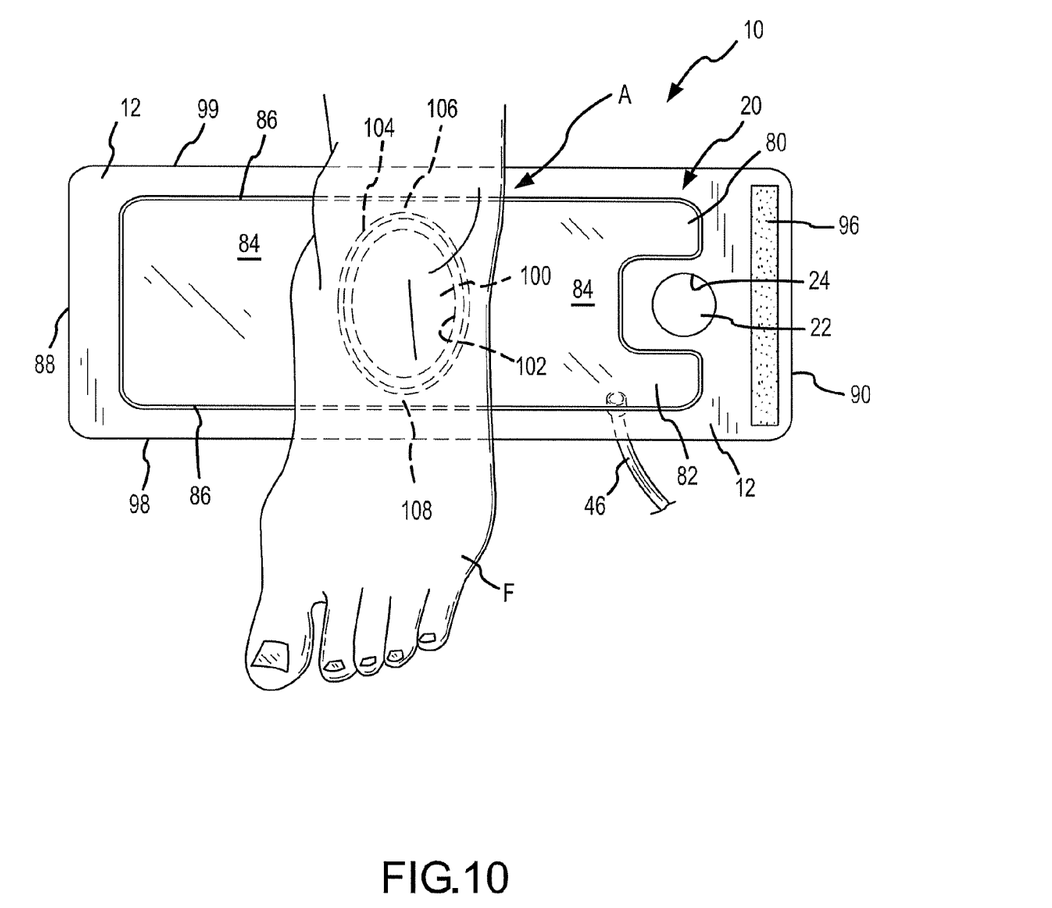
FIG. 10 is a perspective view of yet another embodiment of the present invention for use with the ankle joint.
Figure 11:
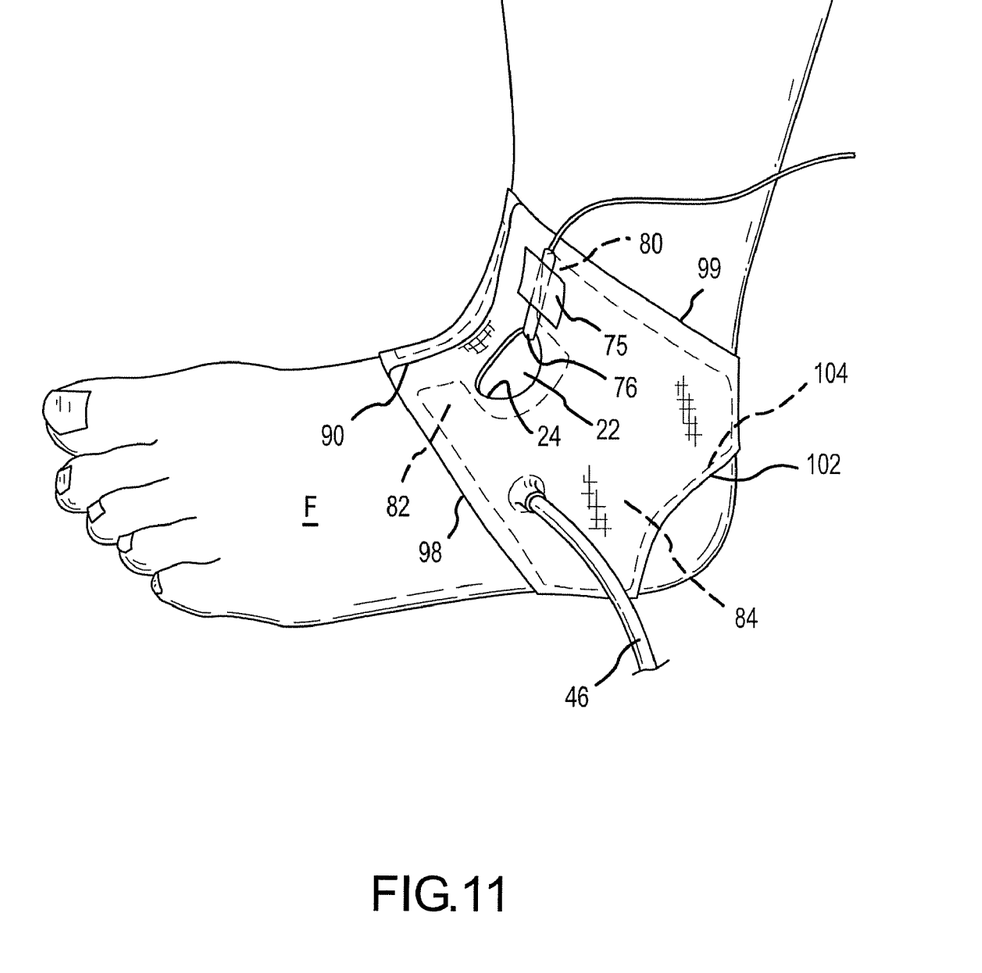
FIG. 11 is another perspective view of the embodiment of FIG. 10 illustrating the device installed on a patient's ankle.

FIGS. 10 and 11 illustrate yet another embodiment of the present invention wherein the device 10 is especially adapted for use with the ankle joint A. The shape of the device 10 in this embodiment is very similar to the embodiment shown in FIGS. 8 and 9 in that the main panel 12 is rectangular shaped; however, this embodiment does not include an extension 92 and rather includes a central opening 100 defined by edge 102 that accommodates the heel of the patient. The same reference numbers used in this embodiment correspond to the same structural features in the embodiment of FIGS. 8 and 9. Accordingly, the device 10 in this embodiment also includes respective transverse edges 98 and 99, respective longitudinal edges 88 and 90, and hook and pile material 96 for securing the device to the patient's ankle. The inflatable bladder 20 also includes the main portion 84, along with the pair of extensions 80 and 82 that surround the access opening 22. Because of the opening 100, the bladder also has an opening or aperture defined by border 104, yet the entire main portion 84 is inflatable since connecting channels 106 and 108 communicate with both lateral sides of the main portion 84. As with the embodiment of FIG. 8, the arrangement of the inflatable bladder 20 results in circumferential pressure being placed around the ankle such that joint fluid is displaced and concentrated at the access opening 22.

Although the embodiments of FIGS. 8-11 illustrate only one access opening 22, it shall be understood that these embodiments can also be modified in the same manner as the embodiment of FIG. 6 such that more than one access opening is provided enabling the practitioner to choose among two locations for aspiration of the joint. The access opening that is not used can be plugged with a pressurizing element like plug 54 thereby maintaining uniform and continuous pressure on the joint except where aspiration is to be performed.

Additionally, although FIGS. 8-11 do not specifically illustrate use of an additional layer of fabric material 23, it shall also be understood that the inflatable bladders in these embodiments may be secured in a pocket defined by the space between an additional layer 23 and the main panel like shown in the embodiment of FIG. 3.

While the present invention has been disclosed above with respect to various preferred embodiments, it shall be understood that changes and modifications may be made to the invention in accordance with the scope of the claims appended hereto.

What is claimed is:

1. A joint aspirate facilitating device comprising:
a main panel having first and second transverse edges and first and second longitudinal edges as said main panel is oriented with respect to a joint of a patient;
an inflatable bladder secured to an interior side of said main panel, said inflatable bladder being oriented to compress at least one fluid sac of the joint, said inflatable bladder having a main portion with a generally curved configuration, said inflatable bladder further including a pair of transverse extensions protruding from said main portion and a converging area located between said pair of extensions and said main portion, said bladder extending between said longitudinal edges of said main panel;
at least one access opening formed in said main panel, said access opening located at a targeted area where joint fluid is to be aspirated from the joint, said at least one access opening being formed in a gap between said pair of extensions, said extensions terminating adjacent said at least one access opening such that said extensions do not encircle the access opening;
a closure element secured to at least one of said first and second longitudinal edges for is tightly securing the device to the joint.

2. A device, as claimed in claim 1, further including:
means for selectively pressurizing said bladder and placed in fluid communication with said bladder.

3. A device, as claimed in claim 2, wherein:
said means for selectively pressurizing includes a hand pump communicating with said bladder.

4. A device, as claimed in claim 2, wherein:
said means for selectively pressurizing includes a viscous gel material placed in said bladder.

5. A device, as claimed in claim 2, further including:
a pressure gauge placed in fluid communication with said means for pressurizing.

6. A device, as claimed in claim 1, further including:
an alignment indicator formed on an exterior surface of said main panel for aligning said device with respect to the joint.

7. A device, as claimed in claim 6, wherein:
said alignment indicator is a line substantially conforming to a shape of the kneecap.

8. A device, as claimed in claim 6, wherein:
said alignment indicator is a patch of material having a thickness that is less than a thickness of said main panel.

9. A device, as claimed in claim 6, wherein:
said alignment indicator is a transparent material.

10. A device, as claimed in claim 6, wherein:
said alignment indicator includes an additional opening formed in said main panel for exposing a portion of the joint.

11. A device, as claimed in claim 1, wherein:
one of said first and second longitudinal edges includes a curved shape flap formed thereon.

12. A device, as claimed in claim 1, further including:
means for selectively deflating said bladder placed in fluid communication with said bladder.

13. A device, as claimed in claim 1, further including:
a sterile dressing placed around said at least one access opening.

14. A device, as claimed in claim 13, wherein:
said dressing is ring-shaped.

15. A device, as claimed in claim 1, further including:
an additional layer of material secured to said interior side of said main panel and forming a pocket, wherein said bladder is removably secured in said pocket.

16. A device, as claimed in claim 1, further including:
a sleeve secured to an exterior surface of said main panel, said sleeve being especially adapted for receiving an ultrasound transducer.

17. A device, as claimed in claim 1, wherein:
said main portion of said inflatable bladder has a substantially rectangular shape.

18. A device, as claimed in claim 1, wherein:
said generally curved configuration of said main portion of said inflatable bladder is cylindrical shaped.

19. A device, as claimed in claim 1, wherein:
said main panel is rectangular shaped.

20. A device, as claimed in claim 1, wherein:
said main panel further includes a thumb extension protruding from said main panel and said thumb extension having a thumb hole formed therein and especially adapted for receiving a thumb of the patient.

21. A device, as claimed in claim 1, wherein:
said main panel further includes a central opening formed therein and especially adapted for receiving a heel of a patient.

22. A device, as claimed in claim 21, wherein:
said inflatable bladder has an aperture formed therein and surrounding said central opening of said main panel.

23. A device, as claimed in claim 22, wherein:
said inflatable bladder has a pair of channels interconnecting lateral sides of said main portion and said pair of channels being located on opposite ends of said aperture.

24. A method of aspirating a joint, said method comprising the steps of:
providing a device as set form in claim 1;
orienting the device on the joint such that the access opening defines a location where the joint is to be aspirated, and wherein said inflatable bladder is oriented to compress a fluid sac surrounding the joint;
pressurizing the inflatable bladder causing joint fluid to be displaced to the area where the joint is to be aspirated at said access opening, wherein said fluid located at said access opening is increased in volume and fluid pressure as compared to said fluid located at said access opening prior to said pressurizing step; and
aspirating the joint by inserting a needle into the patient at the location of the access opening.

25. A method of displacing fluid in a joint, said method comprising the steps of
  providing a device as set forth in claim 1;
  orienting the device on the joint such that the access opening defines a location where the joint fluid is to be directed, and wherein said inflatable bladder is oriented to compress a fluid sac surrounding the joint; and
  pressurizing the inflatable bladder causing joint fluid to be displaced to the area at said access opening, wherein said fluid located at said access opening is increased in volume and fluid pressure as compared to said fluid located at said access opening prior to said pressurizing step.

26. Joint aspirate facilitating device comprising:
  a main panel having first and second transverse edges and first and second longitudinal edges as said main panel is oriented with respect to a joint of a patient;
  an inflatable bladder secured to an interior side of said main panel and oriented to compress at least one fluid sac of the joint, said bladder having a pair of legs extending transversely and substantially parallel to one another, said legs having a first end connected to a first transverse side of said bladder, said first transverse side including converging side edges terminating at a small end, said legs having a second end connected to a second transverse side of said bladder, said second transverse side terminating with a rounded shape;
  at least one access opening formed in said main panel, said access opening located at a targeted area where joint fluid is to be aspirated from the joint;
  a closure element secured to at least one of said first and second longitudinal edges for tightly securing the device to the joint.

27. A joint aspirate facilitating device comprising:
  a main panel having first and second transverse edges and first and second longitudinal edges as said main panel is oriented with respect to a joint of a patient;
  an inflatable bladder secured to an interior side of said main panel, said inflatable bladder being oriented to compress at least one fluid sac of the joint, said inflatable bladder having a first transverse side including converging edges terminating at a small end, and a second transverse side having a rounded shape, and further wherein said bladder has a ring configuration such that a central area is devoid of any bladder material, and a pair of access openings are provided in the central area, said access openings being spaced from one another such that when said device is secured to a patient, said openings are located over medial and lateral sides of a joint; and
  a closure element secured to at least one of said first and second longitudinal edges for tightly securing the device to the joint.

28. A method of aspirating a joint, said method comprising the steps of:
  providing a device as set forth in claim 27;
  orienting the device on the joint such that the access opening defines a location where the joint is to be aspirated, and wherein said inflatable bladder is oriented to compress a fluid sac surrounding the joint;
  pressurizing the inflatable bladder causing joint fluid to be displaced to the area where the joint is to be aspirated at said access opening, wherein said fluid located at said access opening is increased in volume and fluid pressure as compared to said fluid located at said access opening prior to said pressurizing step; and
  aspirating the joint by inserting a needle into the patient at the location of the access opening.

29. A device, as claimed in claim 28, wherein:
  said inflatable bladder includes a central aperture formed therein to accommodate said pair of access openings.

30. A device, as claimed in claim 28, wherein:
  said alignment indicator is positioned between said pair of access openings.

31. A device, as claimed in claim 28, further including:
  a plug selectively placed in one of said pair of access openings.

32. A device, as claimed in claim 28, further including:
  a plug securing flap secured to said main panel and over said plug.

* * * * *

UNITED STATES PATENT AND TRADEMARK OFFICE
CERTIFICATE OF CORRECTION

PATENT NO. : 7,468,048 B2  Page 1 of 1
APPLICATION NO. : 11/539578
DATED : December 23, 2008
INVENTOR(S) : Richard Meehan It is certified that error appears in the above-identified patent and that said Letters Patent is hereby corrected as shown below:

Column 7, Line 47, please delete "is"

Signed and Sealed this

Seventeenth Day of February, 2009

JOHN DOLL
*Acting Director of the United States Patent and Trademark Office*